(12) United States Patent
Bastue et al.

(10) Patent No.: US 11,902,746 B2
(45) Date of Patent: Feb. 13, 2024

(54) EAR LEVEL AUDITORY SYSTEM

(71) Applicant: Widex A/S, Lynge (DK)

(72) Inventors: Jens Bastue, Virum (DK); Jakob Nielsen, Copenhagen (DK); Eline Borch Petersen, Helsingoer (DK)

(73) Assignee: Widex A/S, Lynge (DK)

( * ) Notice: Subject to any disclaimer, the term of this patent is extended or adjusted under 35 U.S.C. 154(b) by 161 days.

(21) Appl. No.: 17/607,687

(22) PCT Filed: Apr. 30, 2020

(86) PCT No.: PCT/EP2020/062140
§ 371 (c)(1),
(2) Date: Oct. 29, 2021

(87) PCT Pub. No.: WO2020/221898
PCT Pub. Date: Nov. 5, 2020

(65) Prior Publication Data
US 2022/0217476 A1     Jul. 7, 2022

(30) Foreign Application Priority Data

May 1, 2019   (DK) .............................. PA201900525

(51) Int. Cl.
*H04R 25/00*     (2006.01)
*A61B 5/00*      (2006.01)

(52) U.S. Cl.
CPC ......... *H04R 25/505* (2013.01); *A61B 5/4812* (2013.01); *H04R 25/552* (2013.01); *H04R 25/554* (2013.01); *H04R 25/603* (2019.05); *H04R 25/604* (2013.01); *H04R 2225/39* (2013.01); *H04R 2225/41* (2013.01); *H04R 2460/11* (2013.01)

(58) Field of Classification Search
CPC ............ H04R 2225/39; H04R 2225/41; H04R 2225/61; H04R 2460/11; H04R 25/02; H04R 25/505; H04R 25/552; H04R 25/554; H04R 25/558; H04R 25/603; H04R 25/604
USPC ......................................................... 381/315
See application file for complete search history.

(56) References Cited

U.S. PATENT DOCUMENTS

| | | |
|---|---|---|
| 6,816,599 B2 | 11/2004 | Thiede et al. |
| 2013/0202119 A1 | 8/2013 | Thede |
| 2015/0092971 A1 | 4/2015 | Kim |
| 2015/0164361 A1 | 6/2015 | Lunner |
| 2016/0261962 A1 | 9/2016 | Petersen et al. |
| 2017/0173296 A1 | 6/2017 | Park et al. |
| 2017/0340855 A1 | 11/2017 | Soulet De Brugiere et al. |
| 2018/0133504 A1 | 5/2018 | Malchano et al. |

FOREIGN PATENT DOCUMENTS

| | | |
|---|---|---|
| EP | 2 071 872 A1 | 6/2009 |
| WO | 2014/162286 A1 | 10/2014 |

OTHER PUBLICATIONS

Danish first technical examination for PA 2019 00525, dated Oct. 30, 2019.
Written Opinion for PCT/EP2020/062140, dated Jul. 21, 2020.
International Search Report for PCT/EP2020/062140, dated Jul. 21, 2020.

*Primary Examiner* — Phylesha Dabney
(74) *Attorney, Agent, or Firm* — Sughrue Mion, PLLC

(57) ABSTRACT

An ear level auditory system comprising at least one ear level audio device (110, 210) adapted to provide a treatment based on inducing neural oscillations in a user.

18 Claims, 2 Drawing Sheets

EAR LEVEL AUDITORY SYSTEM

FIELD OF THE INVENTION

The present invention relates to an ear level auditory system.

BACKGROUND OF THE INVENTION

An ear level auditory system may comprise one or two ear level audio devices. In this application, an ear level audio device should be understood as a small, battery-powered, microelectronic device designed to be worn in or at an ear of a user. The ear level audio device generally comprises an energy source such as a battery or a fuel cell, at least one microphone, an internal sound generator, a microelectronic circuit comprising a digital signal processor, and an acoustic output transducer. The ear level audio device is enclosed in a casing suitable for fitting in or at (such as behind) a human ear.

U.S. Pat. No. 6,816,599 B2 discloses an internal sound generator in the form of a music synthesizer.

If the ear level audio device furthermore is capable of amplifying an ambient sound signal in order to alleviate a hearing deficit the ear level audio device may be considered a personal sound amplification product or a hearing aid.

According to variations the mechanical design of an ear level audio device may resemble those of hearing aids and as such traditional hearing aid terminology may be used to describe various mechanical implementations of ear level audio devices that are not hearing aids. As the name suggests, Behind-The-Ear (BTE) hearing aids are worn behind the ear. To be more precise, an electronics unit comprising a housing containing the major electronics parts thereof is worn behind the ear. An earpiece for emitting sound to the hearing aid user is worn in the ear, e.g. in the concha or the ear canal. In a traditional BTE hearing aid, a sound tube is used to convey sound from the output transducer, which in hearing aid terminology is normally referred to as the receiver, located in the housing of the electronics unit and to the ear canal. In more recent types of hearing aids, a conducting member comprising electrical conductors conveys an electric signal from the housing and to a receiver placed in the earpiece in the ear. Such hearing aids are commonly referred to as Receiver-In-The-Ear (RITE) hearing aids. In a specific type of RITE hearing aids the receiver is placed inside the ear canal. This category is sometimes referred to as Receiver-In-Canal (RIC) hearing aids. In-The-Ear (ITE) hearing aids are designed for arrangement in the ear, normally in the funnel-shaped outer part of the ear canal. In a specific type of ITE hearing aids the hearing aid is placed substantially inside the ear canal. This category is sometimes referred to as Completely-In-Canal (CIC) hearing aids or Invisible-In-Canal (IIC). This type of hearing aid requires an especially compact design in order to allow it to be arranged in the ear canal, while accommodating the components necessary for operation of the hearing aid.

It has been suggested that a multitude of different defective health conditions may be at least alleviated using auditory stimulation.

As one example, WO-A1-2014162286 discloses that psychological/psychiatric and neurological disorders such as sleep disorders/insomnia, anxiety, panic attacks, depression, obsessive-compulsive disorders, schizophrenia and neurological disorders such as headaches/migraines, tinnitus, diplopia, dementia, autism spectrum, Alzheimer's Disease and Pick's disease may be treated using auditory stimulation.

Additionally, WO-A1-2014162286 also discloses that physical and psychological peak performance in healthy subjects may be improved using auditory stimulation.

However, the usability of present systems for providing suitable auditory stimulation, still needs improvement especially when long term treatment of patients with severe neurological disorders such as Alzheimer's Disease is considered and when treatment of patients with several psychological/psychiatric disorders is considered.

SUMMARY OF THE INVENTION

It is therefore an object of the present invention to provide an ear level auditory system and a method and a method of operating an ear level auditory system that are both improved with respect to long term auditory stimulation for alleviating psychological/psychiatric and neurological disorders or for improving physical and psychological peak performance.

The invention, in a first aspect, provides an ear level auditory system according to claim 1.

This provides an ear level auditory system that is advantageous with respect to at least long term treatments and for ease of use.

Further advantageous features appear from the dependent claims.

Still other objects of the present invention will become apparent to those skilled in the art from the following description wherein the invention will be explained in greater detail.

BRIEF DESCRIPTION OF THE DRAWINGS

The invention will be readily understood from the following detailed description in conjunction with the accompanying drawings. As will be realized, the invention is capable of other different embodiments, and its several details are capable of modification in various, obvious aspects all without departing from the invention. Accordingly, the drawings and descriptions will be regarded as illustrative in nature and not as restrictive. In the drawings.

DETAILED DESCRIPTION

In the present context an ear level auditory system may comprise a single ear level audio device or two ear level audio devices—one for both the left and right ear of the user.

In the following the terms neurological disorder and neurological pathology may be used interchangeably.

Figure 1:
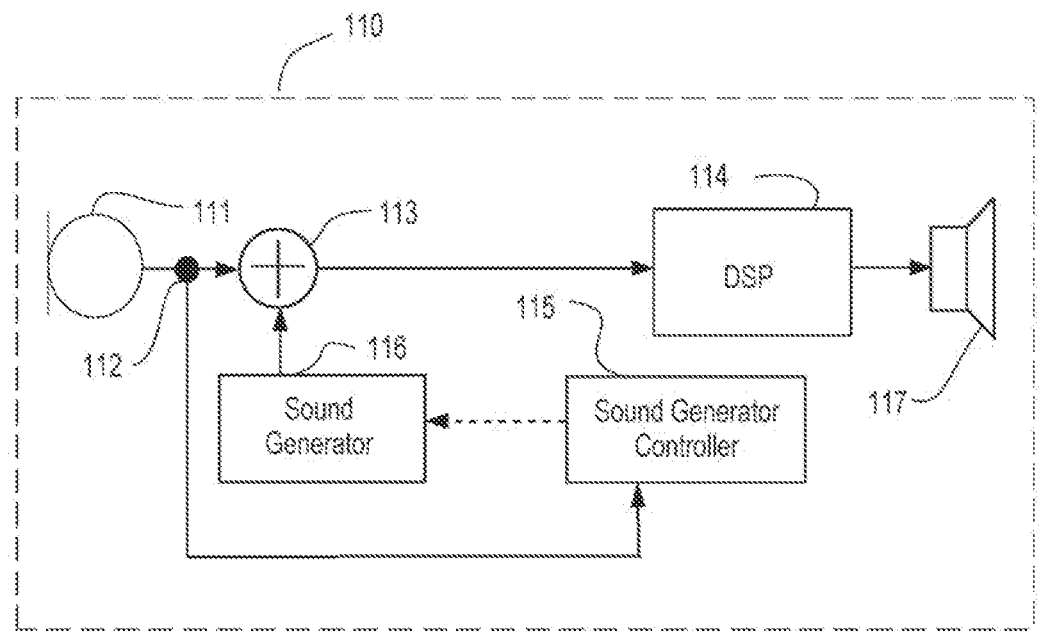
FIG. 1 shows a highly schematic and simplified block diagram of an ear level auditory system consisting of an ear level audio device according to an embodiment of the present invention.

Reference is now made to FIG. 1, which illustrates highly schematically an ear level auditory system according to an embodiment of the invention. The ear level auditory system consists of an ear level audio device 110 that comprises a microphone 111, a branching point 112, a summing unit 113, a digital signal processor (DSP) 114, a sound generator controller 115, a sound generator 116 and an electrical-acoustical output transducer 117.

The microphone 111 provides a microphone signal that is initially provided to the branching point 112 and from there further on to both the summing point 113 and to the sound generator controller 115.

The sound generator controller 115 is configured to control the sound generator 116 and this involves determining the type of auditory stimulation to be provided and when the auditory stimulation is initiated and terminated.

The sound generator 116 is configured to provide at least one type of auditory stimulation adapted to induce neural oscillations, in the frequency range between 0.5 and 100 Hz, in a brain region of a user of the ear level auditory system.

The specific characteristics, of a given auditory stimulation, are determined by a set of sound generator parameters. The specific characteristics include at least: the desired frequency of the induced neural oscillations and the type of auditory stimulation.

The various types of auditory stimulation include at least: binaural beats, monaural beats, isochronic tones and amplitude modulation of various forms of sound.

According to the present embodiment the initiation of the auditory stimulation is carried out in response to an identification of a specific sound environment, which is characterized by speech and music being absent and/or that the noise level is below a certain predetermined threshold, whereby it may be concluded that the auditory stimulation will most likely not disturb the user.

According to a variation the initiation of the auditory stimulation is programmed to start at a specific time of day (or several times during the day) or at a certain time after powering up of the ear level audio device.

According to other variations a detection that the user is walking or lying down may be used as trigger event for initiating the auditory stimulation. According to one specific variation this kind of detection may be carried out using an accelerometer implemented in the ear level audio device 110.

According to yet another variation the initiation of the auditory stimulation is triggered by a detection of the user being in a specific sleep state.

These methods for initiating an auditory stimulation are all advantageous in that they may be carried out without requiring any user interaction, which is essential if the induced neural oscillations are directed at alleviating or treating health deficits, such as neurological disorders, that make the user incapable of administering the auditory stimulation.

According to a specific variation, a multitude of at least some of the above given methods of initiating the auditory stimulation will be available for selection by the user, the device manufacturer or a person responsible for the treatment provided by the induced neural oscillations. In further specific variations it may be selected to initiate the auditory stimulation a multitude of times during the day or during the night and this may be done using the same or different initiation methods.

In a similar manner, according to the present embodiment, the termination of an auditory stimulation is carried out in response to a detection of speech generally, or own voice, or music or an alarm in the sound environment of the user.

According to a variation the termination of an auditory stimulation is programmed to end at a specific time of day (or several times during the day) or at a certain time after initiating the auditory stimulation.

According to yet other variations at least one of the duration and termination of the auditory stimulation is controlled by at least one of a detection of the user being in a specific sleep state for a predetermined duration and a detection of the user transitioning from one sleep stage to another.

According to an embodiment the initiation of the auditory stimulation will be repeated until a specified desired duration of auditory stimulation (which in the following may also be denoted treatment) has been obtained. Thus if repeated treatments are carried out the termination of the treatment will adjusted accordingly. Hereby the duration of the treatment can be controlled even if the user is interrupted while receiving the treatment.

As for the methods for initiating an auditory stimulation the methods for terminating an auditory stimulation are likewise all advantageous in that they may be carried out without requiring any user interaction.

The signals from the sound generator 116 and the microphone 111 are combined in the summing point 113 and provided to the DSP 114 that in turn provides the combined and signal processed electrical signal to the electrical-acoustical output transducer 117 that provides the desired sound to the user and hereby induces neural oscillations in a brain region of the user.

The DSP 114 is configured to apply traditional sound processing such as e.g. noise reduction. According to one especially advantageous variation the DSP 114 is adapted to alleviate a hearing deficit of a user of the ear level auditory system by amplifying the microphone signal.

In other variations both noise reduction and hearing deficit alleviation may be omitted. In yet other variations the microphone is omitted, or the summing point 113 is replaced by a switch such that either the microphone signal or the sound generator signal is used. Alternatively, the microphone is muted or suppressed relative to the sound generator signal when the auditory stimulation (adapted to induce the neural oscillations) is active.

According to another variation the ear level audio device 110 comprises a vent with a variable diameter, that is controllable from the sound generator controller 115, such that the size of the vent diameter is decreased in response to an initiation of the auditory stimulation and to return to normal size in response to a termination of the auditory stimulation.

This is advantageous since a decreased vent diameter generally improves the capability of the ear level audio device to provide sound at low frequencies, which may be required for some of the auditory stimulation types considered in the present context.

However, a decreased vent diameter is likewise advantageous because it suppresses noise or other disturbing sounds from the sound environment, which may be beneficial with respect to the user's ability to pay attention to the provided auditory stimulation. On the other hand it is generally considered to improve wearing comfort when having a vent that is as open as possible and therefore it is advantageous to increase the vent diameter again when the auditory stimulation is terminated.

It is noted that the control of the variable vent is automatic, which is advantageous for the same reasons already given above with respect to the initiation and termination of the auditory stimulation.

Figure 2:
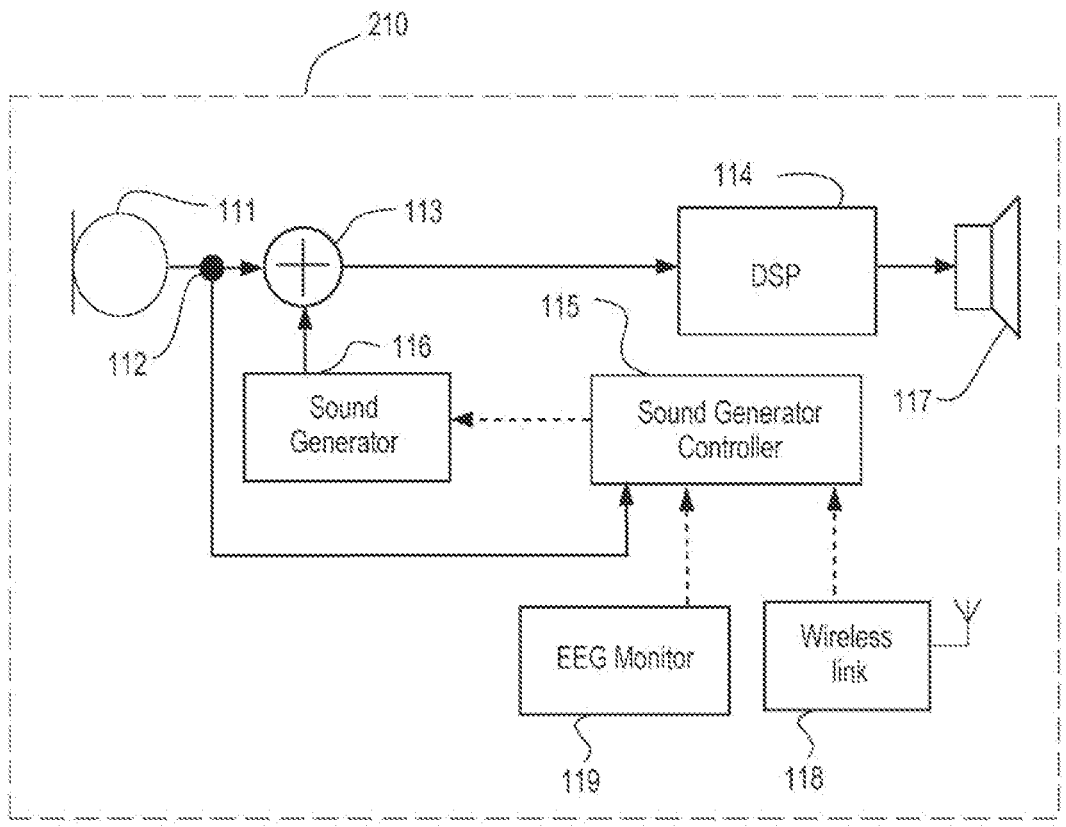
FIG. 2 illustrates highly schematically an ear level auditory system according to an embodiment of the invention.

Reference is now given to FIG. 2 which illustrates highly schematically an ear level auditory system according to an embodiment of the invention. The ear level auditory system consists of an ear level audio device 210 that is similar to the already disclosed ear level audio device 110 except in that a first wireless link means 118 and an EEG monitor 119 have been added (the remaining elements of the ear level audio device have maintained their reference signs).

According to the present embodiment the first wireless link means 118 is configured to enable an operational connection to a remote computer or a remote server. This enables the sound generator controller 115 to be at least partly controlled remotely and the wireless link means 118 also enables that data logged by the ear level audio device 210 can be transmitted to the remote computer or server.

The first wireless link means 118 may be configured to enable direct access to the internet using e.g. some form of cellular mobile communications, such as 4G or 5G. Alternatively the access to the internet may be enabled using an associated external device as gateway, hereby a lower power consumption may be achieved at the cost of requiring that the user of the ear level auditory system has access to such an external device, which typically will be a smart phone.

The ear level auditory system according to the present embodiment is particularly attractive because it allows e.g. a medical doctor to remotely control the auditory stimulation provided to the user of the ear level auditory system. Especially when induced neural oscillations are used for alleviating a defective health condition (or the suitability of using auditory stimulations for such a treatment is tested) it is important that said medical doctor can remotely control the characteristics of the treatment and in particular the intended frequency of the induced neural oscillations, the type of auditory stimulation, the trigger event selected to initiate an auditory stimulation and the duration (which typically will include the trigger event selected to terminate providing said auditory stimulation).

Furthermore, according to a variation the ear level auditory system may be adapted to wirelessly communicate with an associated external device, such as a smart phone, which, as already disclosed above, may be adapted to function as a gateway to a remote server or computer. However, in further variations the associated external device may also be configured to enable interaction with the ear level auditory system using software applications adapted to provide, typically for the user or a not remote health care professional, a similar functionality as disclosed above with reference to the remote control of the ear level auditory system. In variations this functionality will be limited such that only control of parameters that don't require supervision of a health care professional are enabled.

In yet other variations the associated external device may be used to provide various forms of user feedback in response to a provided auditory stimulation. In case the auditory stimulation is directed at treating or alleviating cognitive decline e.g. as a result of Alzheimer's disease or other kinds of dementia, then the provided user feedback may be selected from a group comprising: carrying out online a test directed at evaluating the progress of cognitive decline, such as the Saint Louis University Mental Status examination (SLUMS), using a mental training app capable of evaluating the cognitive health of the user based on the training results and answering an online questionnaire including e.g. the user's subjective evaluation of the effectiveness of the provided auditory treatment or the user's evaluation of success with respect to maintaining focus on the provided auditory treatment, since this at least for some users appear important in order to successfully inducing neural oscillations.

This is advantageous because the wireless connection between the ear level auditory system and the associated external device may be identified and therefore used to link a specific user to a specific associated external device, whereby a system allowing the provision of such types of user feedback to e.g. a medical doctor is facilitated.

However, in addition to determining the sound generator parameters and the relevant trigger events the ear level auditory system according to the present embodiment likewise enables said medical doctor to monitor the provided auditory stimulation adapted to induce neural oscillations by receiving relevant logged data such as duration of the auditory stimulation, time of day of initiation and termination of the auditory stimulation, the sound generator parameters used to determine the type and characteristics (such as the desired frequency of the induced neural oscillations) of the auditory stimulation. Obviously, the data log may cover several independent auditory stimulations, e.g. in case the logged data are not transmitted every day or in case a multitude of auditory stimulations are provided a day.

According to a variation the sound generator controller is configured to allow two or more different auditory stimulations to be active in the ear level auditory system. The different auditory stimulations will differ at least with respect to the desired frequency of the induced neural oscillations, the initiation of—and termination of the auditory stimulation. Hereby the ear level auditory system enables that different types of health deficits may be treated using only a single apparatus. However, in order for this to be enabled the sound generator controller needs to be configured to ensure that the different auditory stimulations do not overlap in time. According to a variation this may be obtained by specifying the exact time of day of initiation and termination of the respective auditory stimulations.

This variation is particularly advantageous because recent research has at least indicated that a multitude of different health deficits may be treated or at least relieved by using auditory stimulations to induce neural oscillations.

Examples of such health deficits are:
chronic pain that may be treated or alleviated by inducing 5 Hz neural oscillations;
post deployment stress that may be treated or alleviated by inducing neural oscillations in the theta range, i.e. say between 6-10 Hz,
insomnia that may be treated or alleviated by inducing neural oscillations in the range between say 1-8 Hz, and finally
initial testing on mice have suggested that Alzheimer's disease may be treated or alleviated by inducing 40 Hz neural oscillations.

It is noted that at least some of the health deficits mentioned are advantageously combined because treatment or at least alleviation of e.g. insomnia is likely to have a positive effect on stress as well as the other way around. According to another aspect it is noted that many soldiers may suffer from both hearing loss and post deployment stress. According to yet another aspect it is noted that e.g. both hearing loss and Alzheimer's disease depend strongly on age.

Thus, in variations, the ear level auditory system according to the present invention may provide a hearing impaired user, already wearing a hearing aid with added value by offering treatment or alleviation of other health deficits.

According to one variation this multi-purpose ear level auditory system may be configured by programming the sound generator controller, when the ear level auditory system is purchased, to administer the auditory stimulations to be provided to the specific user. This scenario may be typical when the ear level auditory system also provides hearing loss compensation.

However, according to another variation, that in fact may as well also apply to ear level auditory systems with hearing loss compensation, additional types of auditory stimulation may be added and activated over time by allowing the sound generator controller to be remotely controlled using the first wireless link means.

According to a variation the sound generator controller is adapted to ensure that a request to remotely control at least one of said two auditory stimulations is correctly authorized.

Figure 3:
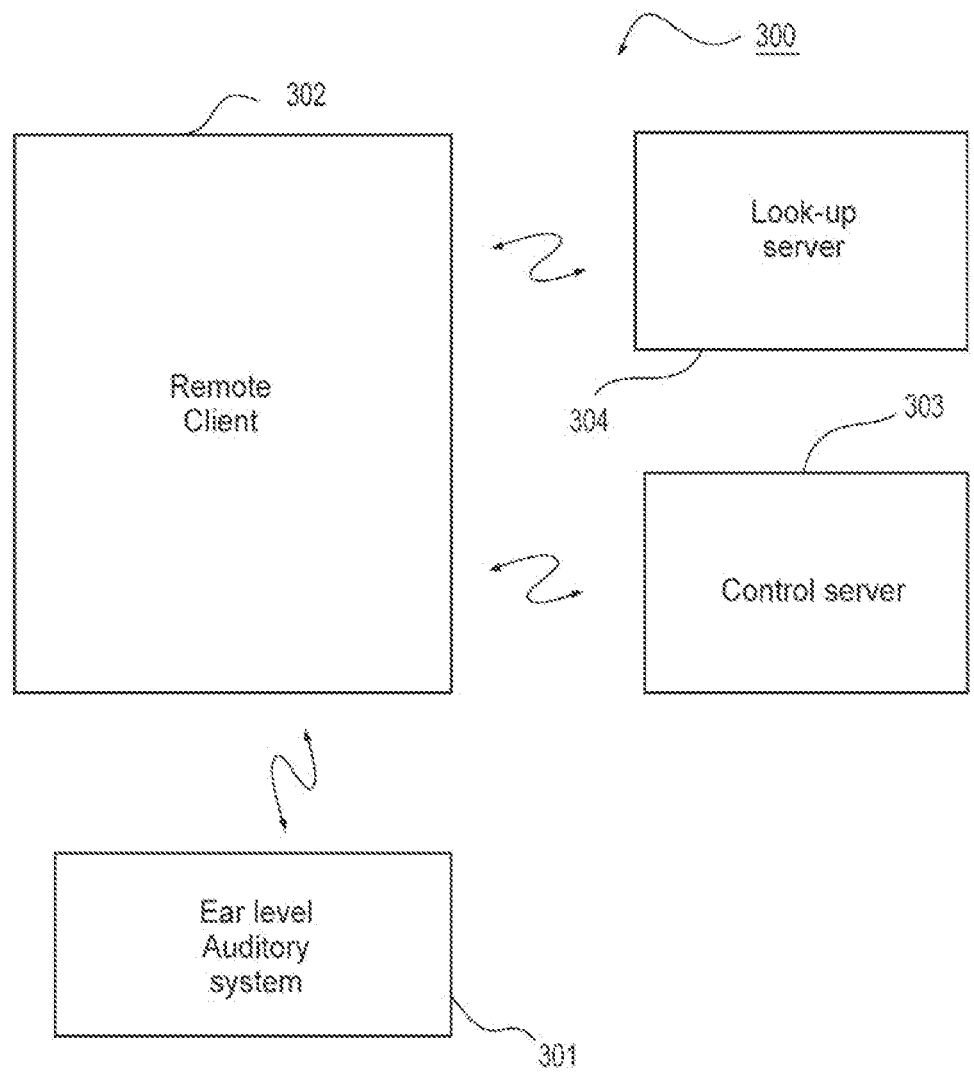
FIG. 3 illustrates highly schematically a remote system for remotely controlling an ear level auditory system according to an embodiment of the invention.

Reference is now made to FIG. 3 for illustrating a remote auditory stimulation system 300 for remotely controlling an ear level auditory system 301 according to an embodiment of the invention.

The remote auditory stimulation system 300 comprises an ear level auditory system 301, a remote client 302, a control server 303, a look-up server 304 and link means, enabling these to communicate.

The look-up server 304 is configured to allow a unique ear level auditory system identification to be searched and subsequently selected, by a remote client 302, based e.g. on the name of the ear level auditory system user.

Thus the ear level auditory system 301 holds a unique ear level auditory system identification and comprises software application means adapted to provide said unique ear level auditory system identification and the associated current ear level auditory system network address to the control server 303 with regular or irregular intervals or based on a given trigger event such as a detection that the current ear level auditory system network address has changed.

The remote client 302 comprises software adapted to at least partly remotely control the sound generator controller of the ear level auditory system 301, whereby at least type, desired frequency of neural oscillations and initiation and duration of an auditory stimulation may be controlled.

The remote client 302 also comprises software adapted to access the look-up server 304 in order to select an unique ear level auditory system identification.

Finally the remote client 302 also comprises software to provide to said control server 303 the associated current remote client network address, the selected unique ear level auditory system identification and a unique remote client operator identification and to request the control server 303 to establish a direct communication channel between said remote client 302 and the ear level auditory system 301 having said selected unique ear level auditory system identification and also taking into account the unique remote client operator identification.

The control server 303 is configured to provide a direct communication channel between the remote client 302 and the ear level auditory system 301 based on the current associated ear level auditory system—and remote client—network addresses and based on an evaluation of whether a remote client operator holding said unique remote client operator identification is entitled to access the ear level auditory system 301 and if this is the case which specific auditory stimulations are accessible for changes or if the remote client operator is entitled to create and activate a new auditory stimulation to be provided. According to the present embodiment the remote client operator may gain entitlement to create and activate a new auditory stimulation in an ear level auditory system by being able to log in to the control server 303 and the look-up server 304.

Furthermore, when a new auditory stimulation is created in an ear level auditory system 301 by storing relevant sound generator parameters in a memory comprised in the sound generator controller, then the unique remote client operator identification is likewise stored in an associated memory, and a subsequent request to make changes to the sound generator parameters will then only be authorized if the remote client operator holds the same unique remote client operator identification.

According to the present embodiment the remote client operator is a medical doctor responsible for monitoring and controlling a provided auditory stimulation, but in variations other types of health caretakers or authorized medical professionals may be responsible. According to still further variations even the user may be responsible for specific types of auditory stimulation that don't need to be supervised by authorized medical professionals.

However, in variations other set-ups may be used to ensure that a request to remotely control an auditory stimulation is correctly authorized.

According to the present embodiment the ear level auditory system 301 is operatively connected to the other components of the remote auditory stimulation system 300 using some form of cellular mobile communication, such as 4G or 5G, but in variations the connection to the other components may be through a gateway enabled by e.g. a smart phone.

Furthermore, in another variation, the transmitted data logs are adapted to reflect the situation where two different types of stimulations are administered by two different responsible entities such as medical doctors, i.e. by labelling the logged data such that a server configured to relay the data logs is capable of transmitting the logged data to the entity responsible for the treatment.

According to a variation the ear level auditory system comprises a second ear level audio device, wherein said first and said second ear level audio device both comprises second wireless link means (not shown) configured to enable the first ear level audio device 210 and the second ear level audio device to exchange at least one of synchronization data and sound generator parameters.

The second ear level audio device as well as the exchange of synchronization data between the two ear level audio devices are required in order to providing binaural beats. However, all types of auditory stimulation are expected to generally benefit from being delivered binaurally (i.e. using two ear level audio devices) because the likelihood that the user is paying attention to the auditory treatment will increase. Thus the exchange of synchronization data and sound generator parameters are advantageous also when providing other types of auditory stimulation than binaural beats.

According to an embodiment the EEG monitor 119 comprises an EEG signal processor and an EEG measuring unit having a multitude of electrodes positioned at an outer surface of a part of the ear level audio device, preferably a part of the ear level device positioned in the ear canal, whereby EEG signals of the ear level auditory system user can be measured.

Based on the measured EEG signals the EEG signal processor can be adapted to provide an estimate of the effectiveness of an auditory stimulation with respect to inducing neural oscillations with a desired frequency based on a short term average level of neural oscillations with said desired frequency.

According to another variation the measured EEG signals can be used to indicate the severity or progress of a neurological disorder or deficit based on a longer term average level of a neural oscillation with a specific given frequency. According to a more specific variation the progress of Alzheimer's disease may be estimated by determining the strength of 40 Hz neural oscillations relative to some other neural oscillations, i.e. by considering the neural oscillation spectrum. In the present context the spectrum of neural oscillations may be divided into five main frequency bands: the delta band with frequencies lower than say 4 Hz, the theta band with frequencies between say 4 Hz and 8 Hz, alpha band with frequencies between say 8 Hz and 12 Hz, the beta band with frequencies between say 12 Hz and 30 Hz and the gamma band with frequencies between say 30 Hz and 100 Hz. Thus according to an even more specific variation the evolution over time of the neural oscillation frequency spectrum within said five main frequency bands may be used to indicate Dementia and Alzheimer's disease and also to subsequently monitor the progression of these type of diseases and hereby the effectiveness of a treatment based on an auditory stimulation adapted to induce 40 Hz neural oscillations. According to one variation Alzheimer's disease is correlated with a relative decrease in induced synchronized gamma band neural oscillations compared to the neural oscillations in at least some of the other neural oscillation frequency bands.

However, according to further advantageous variations, different techniques for estimating the progress of Dementia or Alzheimer's disease may be combined in order to improve precision and robustness.

One such technique is based on measuring the gamma band power, while the user is engaging in relaxed cognitive activities selected from a group comprising music listening and story listening, and correlating Alzheimer's disease with a relative increase in gamma band power. The gamma band power is determined as the squared amplitude of a single EEG signal (as opposed to synchronized neural oscillations that represents an association between two or more different EEG electrodes).

Another such technique is based on measuring the 40 Hz steady state response power evoked by a 40 Hz auditory stimulation and correlating Alzheimer's disease with a relative increase in the 40 Hz steady state response power compared to healthy subjects.

Yet another technique is based on detecting a user's own voice, recording the users spoken words and at least some complete sentences and providing these data to further analysis of the linguistic quality and correlating Alzheimer's disease with a relative decrease in quality.

Finally another technique is based on measuring the 40 Hz EEG activity on both the left and right side of the users head and correlating Alzheimer's disease with a difference between the measured signals being below a given threshold when the user is carrying out certain cognitive tasks. Having an ear level auditory system comprising an ear level audio device at both the user's will be especially advantageous for this type of monitoring.

Thus in the present context the terms "short term average" and "longer term average" are to be construed as relative terms with respect to each other.

According to a variation an estimated short term average level is used as bio-feedback for the sound generator controller 155 such that the sound generator parameter values can be adjusted in order to optimize the inducing of neural oscillations.

According to a more specific variation the optimization of the sound generator parameter values may be carried out using a machine learning algorithm.

According to yet another variation the ear level auditory system further comprises a light source, such as an Light Emitting Diode (LED) that is accommodated in a part of the ear level audio device adapted to be positioned in an ear canal of the user such that it can shine light towards the ear drum whereby neural oscillations with a desired frequency may be induced by flickering the light from the LED with the desired frequency. Hereby, a multimodality or combination treatment may be provided, which is expected to enable improved efficiency of the treatment.

In variations the ear level auditory system consists of a first ear level audio device without an LED and a second ear level LED device without an electrical-acoustical output transducer 117, wherein both devices are adapted to be positioned in an ear canal and wherein both comprises wireless link means configured to enable the first and the second ear level device to exchange at least data representing the desired frequency of the neural oscillations to be induced.

In a further variation said LED device is adapted to be worn in a nose, whereby the provided flickering light may access other parts of the brain than the light provided from the ear canal and through the ear drum. By taking advantage of the wireless link means the nose LED device can be made easy to wear and difficult to notice by others.

In yet other variations the auditory system may in addition to the at least one ear level audio device comprises at least one additional device capable of inducing neural oscillations using a stimulation form other than sound (i.e. tactile stimulation) and being controlled using an advanced version of the sound generator controller and through a wireless connection between the ear level audio device and said at least one additional device. According to a more specific variation the ear level audio device is configured to be at least partly remotely controlled using wireless link means adapted to enable an operational connection to a remote computer or tablet, a remote smart phone or a remote server, whereby e.g. a medical doctor can control the multimodality treatment using either of said remote devices.

According to yet another variation the additional device may comprise implanted electrodes for deep brain stimulation, whereby brain regions that are not easily stimulated by any of the above mentioned modalities become accessible. Thus according to one embodiment an ear level auditory system adapted to also provide deep brain stimulation and capable of being remotely controlled is hereby provided.

According to another variation the ear level auditory system is adapted to enable a performance verification of the provided auditory stimulation to be carried out (i.e. controlled) from a remote computer or remote server using the internet. This variation is attractive because it allows e.g. a medical doctor to verify that the ear level auditory system is performing as expected before providing the auditory stimulation. According to more specific variations the performance verification comprises at least one of an evaluation of the amount of ear wax congestion of the ear level audio devices of the auditory system and of whether the sound pressure level provided by the ear level audio devices are as expected, which typically will include a verification of microphone performance since a microphone of the ear level audio device will typically be required to estimate the provided sound pressure level.

Examples of such methods for audio device performance verification may be found in un-published Danish patent applications PA201800275, PA201800278 and PA201800277. According to another specific variation a system performance verification is required in order to change a setting such as a sound generator parameter.

Furthermore, the value of data to be used in various big data and machine learning contexts may be improved when such a verification is carried out. According to variations big data and machine learning may be used for improving the initially selected auditory stimulation characteristics for a user based on the experience and preferences of other similar users or for suggesting alternative characteristics in response to user complaints or in order to personalize the auditory stimulation characteristics to the preferences of the ear level auditory system user. According to a variation data are simply not included in the big data analysis if a system performance verification has not been carried out or is unsuccessful.

It is generally noted that even though many features of the present invention are disclosed in embodiments comprising other features then this does not imply that these features by necessity need to be combined.

As one example the specific characteristics of the auditory stimulation and how it is controlled and adapted with respect to e.g. optimizing a given users attention to the auditory stimulation are generally independent of each other and of the trigger events used to control the initiation and duration of the auditory stimulation. Furthermore, the specific characteristics of the auditory stimulation as well as the optimization of the given user's attention to the auditory stimulation may be carried out based on EEG signals, but may also be carried out without, e.g. based on at least one of active user responses and data from other user's with similar personality characteristics.

Thus in the present context an active user response requires active interaction from the user e.g. by filling out a questionnaire or taking a test, preferably using an internet connected device. On the other hand the general term user response also includes data that does not require any active interaction from the user, such as e.g. measured EEG signals or detection of the users own voice in order to evaluate whether the user is participating in social activities.

The concept of combining auditory and light stimulation by directing light to the brain through either the ear canal or the nostril using an ear level auditory system is also independent of the specific characteristics of the auditory stimulation, independent of the of the trigger events used to control the initiation and duration of the stimulations and independent of the incorporation of an EEG monitor. The same is true for ear level auditory systems comprising a deep brain stimulator.

Similarly the concepts of allowing the ear level auditory device to be remotely controlled e.g. by a medical doctor or even by two different medical doctors with authorization to control different types of auditory and possibly also other types of stimulation are likewise independent of the specific characteristics of the auditory stimulation, how it is controlled and adapted and independent on whether additional stimulation modalities are supported.

However, a first itemized embodiment according the present invention may comprise the following features:

An ear level auditory system comprising:
a first ear level audio device adapted to be worn in or at a first ear of a user and wherein the first ear level audio device further comprises:
first wireless link means configured to enable an operational connection to at least one of an external device, a remote computer and a remote server,
a sound generator configured to provide at least one type of auditory stimulation adapted to induce neural oscillations, in the frequency range between 0.5 and 100 Hz, in a brain region of said user and wherein the type of auditory stimulation is determined by a set of sound generator parameters, and a sound generator controller adapted to control the type, initiation and termination of said auditory stimulation without requiring user interaction and wherein the sound generator controller is further adapted to at least one of:
be at least partly controlled remotely, and
transmit logged data to a remote computer.

It is noted that the combination of remote control and data logging is especially advantageous because it allows e.g. a medical doctor or similar health care professional to both control and supervise the effect of the auditory stimulation based on user response, wherein especially user response that does not require active user interaction is advantageous for long term treatment and for users with limited cognitive abilities such as e.g. people suffering from Alzheimer and similar diseases.

According to a more specific second itemized embodiment, the ear level auditory system may comprise, in addition to the features of the first embodiment, the following features:
a second ear level audio device, wherein said first and said second ear level audio device comprises:
second wireless link means configured to enable the first and the second ear level audio device to exchange at least one of synchronization data and sound generator parameters, whereby a diotic presentation of the auditory stimulation adapted to induce neural oscillations may be provided based on at least one of said first wireless link and said second wireless link.

A diotic presentation may at least for some people be especially well suited for inducing specific neural oscillations.

According to a more specific third itemized embodiment, the ear level auditory system may comprise, in addition to the features of the first embodiment, the following features:
Likewise, the concept of including an EEG monitor in the ear level auditory system and using it for at least one (and preferably both) of providing bio-feedback in order to control (i.e. change) the specific characteristics of the auditory stimulation in order to maintain a user's attention to the provided stimulation and of providing an estimate of the progression of e.g. Alzheimer' disease by monitoring the induced neural oscillation power spectrum.

Finally, it is noted that in alternative embodiments the remotely controlled features may at least partly be controlled automatically by the auditory system, whereby e.g. the supervision of the auditory treatment and its impact (i.e. the user response) need to be carried out less frequently.

Other modifications and variations of the structures and procedures will be evident to those skilled in the art.

The invention claimed is:

1. An ear level auditory system comprising:
a first ear level audio device adapted to be worn in or at a first ear of a user and wherein the first ear level audio device further comprises:
first wireless link means configured to enable an operational connection to at least one of an external device, a remote computer and a remote server,
a sound generator configured to provide at least one type of auditory stimulation adapted to induce neural oscillations, in the frequency range between 0.5 and 100 Hz, in a brain region of said user and wherein the type of auditory stimulation is determined by a set of sound generator parameters, and
a sound generator controller adapted to control the type, initiation and termination of said auditory stimulation without requiring user interaction and wherein the sound generator controller is further adapted to at least one of:
be at least partly controlled remotely, and
transmit logged data to a remote computer; and
wherein the sound generator controller is further configured to:
allow at least two auditory stimulations to be provided that differ with respect to at least desired frequency of induced neural oscillations, initiation, and termination,
ensure that said two auditory stimulations do not overlap in time.

2. The ear level auditory system according to claim 1, comprising a second ear level audio device, wherein said first and said second ear level audio device comprises:
second wireless link means configured to enable the first and the second ear level audio device to exchange at least one of synchronization data and sound generator parameters.

3. The ear level auditory system according to claim 1, wherein the logged data is selected from a group of data comprising:
duration of the auditory stimulation, time of day of initiation and termination of the auditory stimulation, the sound generator parameters used to determine the type of auditory stimulation and data representing a user response to the auditory stimulation.

4. An ear level auditory system comprising:
a first ear level audio device adapted to be worn in or at a first ear of a user and wherein the first ear level audio device further comprises:
first wireless link means configured to enable an operational connection to at least one of an external device, a remote computer and a remote server,
a sound generator configured to provide at least one type of auditory stimulation adapted to induce neural oscillations, in the frequency range between 0.5 and 100 Hz, in a brain region of said user and wherein the type of auditory stimulation is determined by a set of sound generator parameters, and
a sound generator controller adapted to control the type, initiation and termination of said auditory stimulation without requiring user interaction
and wherein the sound generator controller is further adapted to at least one of:
be at least partly controlled remotely, and
transmit logged data to a remote computer; and
wherein the ear level audio device comprises a vent with a variable diameter that is controllable from the sound generator controller that is adapted to provide that the size of the vent diameter is decreased in response to an initiation of the auditory stimulation and to return to normal size in response to a termination of the auditory stimulation.

5. The ear level auditory system according to claim 1, wherein the type of auditory stimulation is selected from a group comprising: binaural beats, monaural beats, isochronic tones and amplitude modulation of various forms of sound.

6. The ear level auditory system according to claim 1, wherein the initiation of the auditory stimulation is controlled by a trigger event selected from a group of events comprising: identification of a specific sound environment, a specific time of day, a remotely controlled activation, a detection of the user being in a specific sleep state and a detection that the user is walking or lying down.

7. The ear level auditory system according to claim 1, wherein at least one of the duration and termination of the auditory stimulation is controlled by a trigger event selected from a group of events comprising: a predetermined time or duration, a detection of speech or own voice or an alarm in the sound environment of the user, a detection of the user being in a specific sleep state for a predetermined duration and a detection of the user transitioning from one sleep stage to another.

8. The ear level auditory system according to claim 1, further comprising at least one microphone and a digital signal processor configured to alleviate a hearing loss by amplifying an electrical sound signal provided by the at least one microphone.

9. The ear level auditory system according to claim 1, comprising a second ear level audio device, wherein said first and said second ear level audio device comprises:
second wireless link means configured to enable the first and the second ear level audio device to exchange at least one of synchronization data and sound generator parameters, whereby a diotic presentation of the auditory stimulation adapted to induce neural oscillations is provided based on at least one of said first wireless link and said second wireless link.

10. The ear level auditory system according to claim 4, wherein the sound generator controller is further configured to
allow at least two auditory stimulations to be provided that differ with respect to at least desired frequency of induced neural oscillations, initiation, and termination,
ensure that said two auditory stimulations do not overlap in time.

11. The ear level auditory system according to claim 10, comprising a second ear level audio device, wherein said first and said second ear level audio device comprises:
second wireless link means configured to enable the first and the second ear level audio device to exchange at least one of synchronization data and sound generator parameters.

12. The ear level auditory system according to claim 10, wherein the logged data is selected from a group of data comprising:
duration of the auditory stimulation, time of day of initiation and termination of the auditory stimulation, the sound generator parameters used to determine the type of auditory stimulation and data representing a user response to the auditory stimulation.

13. The ear level auditory system according to claim 10, wherein the type of auditory stimulation is selected from a group comprising: binaural beats, monaural beats, isochronic tones and amplitude modulation of various forms of sound.

14. The ear level auditory system according to claim 10, wherein the initiation of the auditory stimulation is controlled by a trigger event selected from a group of events comprising: identification of a specific sound environment, a specific time of day, a remotely controlled activation, a detection of the user being in a specific sleep state and a detection that the user is walking or lying down.

15. The ear level auditory system according to claim 10, wherein at least one of the duration and termination of the auditory stimulation is controlled by a trigger event selected from a group of events comprising: a predetermined time or duration, a detection of speech or own voice or an alarm in the sound environment of the user, a detection of the user being in a specific sleep state for a predetermined duration and a detection of the user transitioning from one sleep stage to another.

16. The ear level auditory system according to claim 10, further comprising at least one microphone and a digital signal processor configured to alleviate a hearing loss by amplifying an electrical sound signal provided by the at least one microphone.

17. A method of operating an ear level auditory system comprising an ear level audio device adapted to be worn in or at a first ear of a user and comprising the steps of:

configuring first wireless link means to enable an operational connection to at least one of an external device, a remote computer and a remote server, configuring a sound generator to provide at least one type of auditory stimulation adapted to induce neural oscillations, in the frequency range between 0.5 and 100 Hz, in a brain region of said user and wherein the type of auditory stimulation is determined by a set of sound generator parameters, adapting a sound generator controller to control the type, initiation and termination of said auditory stimulation without requiring user interaction, adapting the sound generator controller to at least one of:

be at least partly controlled remotely and to transmit logged data to a remote computer, and providing an auditory stimulation under the control of the sound generator controller; and wherein the sound generator controller:

allows at least two auditory stimulations to be provided that differ with respect to at least desired frequency of induced neural oscillations, initiation, and termination; and ensures that said two auditory stimulations do not overlap in time.

18. A non-transitory computer readable medium carrying instructions which, when executed by a computer, cause the method according to claim 17 to be performed.

* * * * *